(12) United States Patent
Neumann

(10) Patent No.: US 12,046,352 B2
(45) Date of Patent: *Jul. 23, 2024

(54) SYSTEM AND METHOD FOR GENERATING A COGNITIVE DISORDER NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN Innovations, LLC, Lakewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/200,635

(22) Filed: May 23, 2023

(65) Prior Publication Data

US 2023/0298735 A1 Sep. 21, 2023

Related U.S. Application Data

(63) Continuation of application No. 17/187,997, filed on Mar. 1, 2021, now Pat. No. 11,694,787.

(51) Int. Cl.
*G16H 20/70* (2018.01)
*G06N 20/00* (2019.01)
*G16H 20/60* (2018.01)

(52) U.S. Cl.
CPC .............. *G16H 20/70* (2018.01); *G06N 20/00* (2019.01); *G16H 20/60* (2018.01)

(58) Field of Classification Search
CPC ......... G16H 20/70; G16H 20/60; G06N 20/00
USPC ................................................. 700/90–212
See application file for complete search history.

(56) References Cited

U.S. PATENT DOCUMENTS

| | | |
|---|---|---|
| 7,187,790 B2 | 3/2007 | Sabol |
| 7,295,889 B2 | 11/2007 | Lahteenmaki |
| 9,710,606 B2 | 7/2017 | Apte |
| 9,936,916 B2 | 4/2018 | Sahin |
| 10,327,641 B2 | 6/2019 | Apte |
| 11,367,519 B1 * | 6/2022 | Heldman .............. A61M 5/142 |

(Continued)

FOREIGN PATENT DOCUMENTS

WO 2020069500 A1 4/2020

OTHER PUBLICATIONS

Sutarto, Auditya Purwandini, Muhammad Nubli Abdul Wahab, and Nora Mat Zin. "Effect of biofeedback training on operator's cognitive performance." Work 44.2 (2013): pp. 231-243. (Year: 2013).*

(Continued)

*Primary Examiner* — Satish Rampuria
(74) *Attorney, Agent, or Firm* — Caldwell Intellectual Property Law

(57) ABSTRACT

A system for generating a cognitive disorder nourishment program comprises a computing device configured to obtain a cognitive indicator element, produce a cognitive appraisal as a function of the cognitive indicator element, wherein producing further comprises identifying a cognitive function as a function of an experience label, and producing the cognitive appraisal as a function of the cognitive function and cognitive indicator element using a cognitive machine-learning model, determine an edible as a function of the cognitive appraisal, and generate a nourishment program as a function of the edible.

16 Claims, 7 Drawing Sheets

(56) References Cited

U.S. PATENT DOCUMENTS

| | | | | |
|---|---|---|---|---|
| 2007/0282912 | A1* | 12/2007 | Reiner | G16H 15/00 |
| 2009/0172773 | A1* | 7/2009 | Moore | G06F 16/958 |
| | | | | 705/2 |
| 2010/0063368 | A1 | 3/2010 | Leuthardt et al. | |
| 2019/0034581 | A1 | 1/2019 | Aliper et al. | |
| 2020/0077939 | A1 | 3/2020 | Richer et al. | |
| 2022/0277827 | A1 | 9/2022 | Neumann | |

OTHER PUBLICATIONS

Svensson, Martina, Jan Lexell, and Tomas Deierborg. "Effects of physical exercise on neuroinflammation, neuroplasticity, neurodegeneration, and behavior: what we can learn from animal models in clinical settings." Neurorehabilitation and neural repair 29.6 (2015): pp. 577-589. (Year: 2015).*

Kotekar, Nalini, Anshul Shenkar, and Ravishankar Nagaraj. "Postoperative cognitive dysfunction—current preventive strategies." Clinical interventions in aging (2018): pp. 2267-2273. (Year: 2018).* https://link.springer.com/article/10.1007/s10916-018-1071-x; Title: Machine learning for predicting cognitive diseases: methods, data sources and risk factors; By: Brati, Brankica; Date: Oct. 27, 2018.

https://www.mdpi.com/1422-0067/20/11/2842; Title: Frailty, cognitive decline, neurodegenerative diseases and nutrition interventions; By: Gomez-Gomez; Date: Jun. 11, 2019.

https://gsconlinepress.com/journals/gscbps/content/functional-foods-and-bioactive-compounds-roles-prevention-treatment-and-management; Title: Roles in the prevention, treatment and management of neurodegenerative diseases; By: Olagunj Abolaji.

https://www.tandfonline.com/doi/abs/10.1080/19390211.2017.1401573; Title: Functional foods and nutraceuticals as dietary intervention in chronic diseases; novel perspectives for health promotion and disease prevention; By: Adefegha, Stephen Adeniyi; Date: Dec. 27, 2017.

https://www.sciencedirect.com/science/article/pii/S0047637413001309; Title: Cognitive decline, dietary factors and gut-brain interactions; By: Caracciolo, Barbara; Date: Dec. 12, 2013.

https://www.ncbi.nlm.nih.gov/pmc/articles/PMC3975244/; Title: Neuroimaging biomarkers of neurodegenerative diseases and dementia; By: Shannon L. Risacher & Andrew J. Saykin; Date: Nov. 14, 2013.

https://www.sciencedirect.com/science/article/pii/S014067361630959X; Title: Diagnosis of multiple sclerosis: progress and challenges; By: Brownlee, Wallace J.; Date: Nov. 24, 2016.

https://www.ncbi.nlm.nih.gov/pmc/articles/PMC6150469/; Title: A novel dynamic hyper-graph inference framework for computer assisted diagnosis of neuro-diseases; By: Zhu, Yingying; Date: May 23, 2017.

https://dl.acm.org/doi/abs/10.1145/3344998; Title: Machine learning techniques for the diagnosis of Alzheimer's disease: A review; By: Tanveer, M.; Date: Apr. 1, 2020.

https://www.hindawi.com/journals/np/2017/3589271/; Title: Lifestyle modulators of neuroplasticity: how physical activity, mental engagement, and diet promote cognitive health during aging; By: Phillips, Christy; Date: Jun. 12, 2017.

* cited by examiner

SYSTEM AND METHOD FOR GENERATING A COGNITIVE DISORDER NOURISHMENT PROGRAM

CROSS-REFERENCE TO RELATED APPLICATIONS

This application is a continuation-in-part of Non-provisional application Ser. No. 17/187,997 filed on Mar. 1, 2021, and entitled "SYSTEM AND METHOD FOR GENERATING A COGNITIVE DISORDER NOURISHMENT PROGRAM," the entirety of which is incorporated herein by reference.

FIELD OF THE INVENTION

The present invention generally relates to the field of artificial intelligence. In particular, the present invention is directed to a system and method for generating a cognitive disorder nourishment program.

BACKGROUND

Current edible suggestion systems do not account for the status of addictions and/or addiction symptoms. This leads to inefficiency of an edible suggestion system and a poor nutrition plan for the individual. This is further complicated by a lack of uniformity of nutritional plans, which results in dissatisfaction of individuals.

SUMMARY OF THE DISCLOSURE

In an aspect, a system for generating a cognitive disorder nourishment program includes a computing device that includes a processor and a memory and is configured to obtain a cognitive indicator element, determine an edible as a function of the cognitive indicator element, generate a nourishment program as a function of the edible, receive a cognitive response of a user as a function of implementing the nourishment program and update the nourishment program as a function of the cognitive response.

In another aspect, a method for generating a cognitive disorder nourishment program includes obtaining, by a computing device, a cognitive indicator element, determining, by the computing device, an edible as a function of the cognitive indicator element, generating, by the computing device, a nourishment program as a function of the edible, receiving, by the computing device, a cognitive response of a user as a function of implementing the nourishment program and updating, by the computing device, the nourishment program as a function of the cognitive response.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a cognitive disorder nourishment program. In an embodiment, this disclosure may obtain a cognitive indicator element that relates to an individual's nervous system. Aspects of the present disclosure may be used to produce a cognitive appraisal that may identify one or more cognitive functions of an individual's nervous system. This is so, at least in part, because this disclosure incorporates a machine-learning model. Aspects of the present disclosure can also be used determine an edible as a function of the cognitive appraisal. Aspects of the present disclosure allow for generating a nourishment program as a function of the determined edible for the cognitive appraisal. Exemplary embodiments illustrating aspects of the present disclosure are described below in the context of several specific examples.

Figure 1:
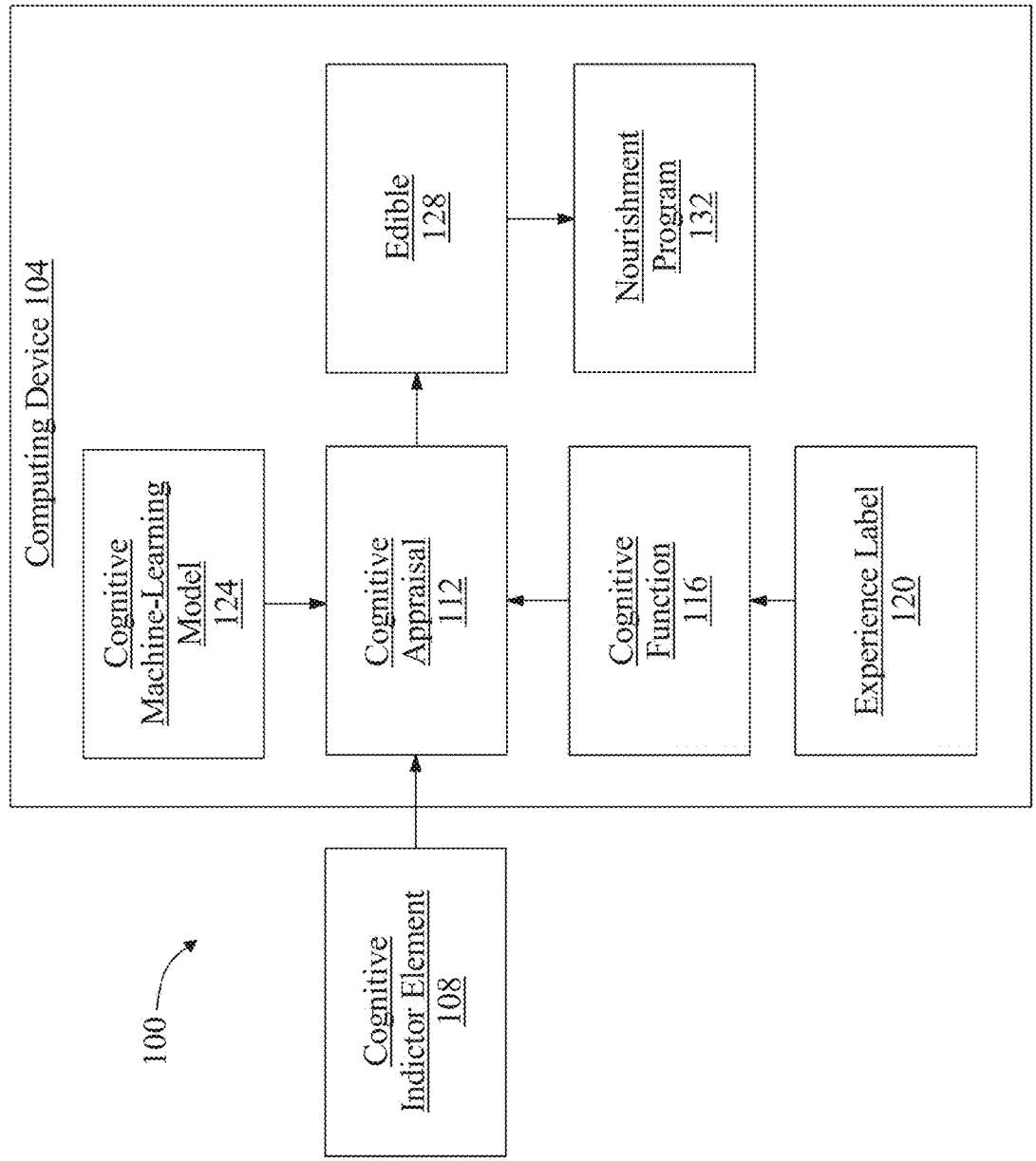
FIG. 1 is a block diagram illustrating an exemplary embodiment of a system for generating a cognitive disorder nourishment program.

Referring now to FIG. 1, an exemplary embodiment of a system 100 for generating a cognitive disorder nourishment program is illustrated. System includes a computing device 104. computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 obtains a cognitive indicator element 108. As used in this disclosure an "cognitive indicator element" is an element of data that denotes the health status of an individual's nervous system. Cognitive indicator element 108 may include a biological sample. As used in this disclosure a "biological sample" is one or more biological specimens collected from an individual. Biological sample may include, without limitation, exhalate, blood, sputum, urine, saliva, feces, semen, and other bodily fluids, as well as tissue. Cognitive indicator element 108 may include a biological sampling device. Cognitive indicator element 108 may include one or more biomarkers. As used in this disclosure a "biomarker" is a molecule and/or chemical that identifies the health status of a user's health system. As a non-limiting example, biomarkers may include, PSEN1, PSEN2, amyloid precursor protein, Beta-amyloid, Phospho-tau 181, SB100, p-tau217, p-tau181, Af342/40 and neurofilament light chain, G-CIMP, N-methyl-D-aspartate receptor, D-dimmer, fibrinogen, fibronectin, von Willebrand factor, thrombomodulin, brain natriuretic peptide (BNP), lipoprotein-associated phospholipase A2, IL-6, TNF-alpha, tau proteins, amyloid B, dopamine metabolism, alpha synuclein, mitochondrial function, Coenzyme Q10 (CoQ10), acetyl-L-carnitine, nicotinamide adenine dinucleotide (NADH), resveratrol and the like thereof. In another non-limiting example, cognitive indicator element 108 may include gut microbiome. For the purposes of this disclosure, "gut microbiome" is a complex community of microorganisms that reside in a gastrointestinal tract. As a non-limiting example, gut microbiome may include bacteria, fungi, viruses, and other microbes. As a further non-limiting example, cognitive indicator element 108 may include datum from one or more devices that collect, store, and/or calculate one or more lights, voltages, currents, sounds, chemicals, pressures, and the like thereof that are associated with the user's nervous system. As used in this disclosure a "nervous system" is an organ and/or tissue system that relates to the nerves and/or transmission of signals in an individual's body. As a non-limiting example, nervous system may include one or more central nervous systems, peripheral nervous systems, somatic nervous systems, autonomic nervous systems, and the like thereof.

Still referring to FIG. 1, computing device 104 may obtain cognitive indicator element 108 by receiving an input from a user. As used in this disclosure "input" is an element of datum that is obtained by the user. In an embodiment, and without limitation, input may include one or more inputs from a family member. For example, and without limitation, a brother, sister, mother, father, cousin, aunt, uncle, grandparent, child, friend, and the like thereof may enter to computing device 104 that an individual may have altered and/or changing nervous system health. Input may include one or more inputs from an informed advisor as a function of identifying a cognitive assessment, wherein a "cognitive assessment" is an evaluation and/or estimation of the health status of the nervous system of the individual. For example, and without limitation, a cognitive assessment may include one or more assessments of memory, behavior, motor function, emotions, and the like thereof. As used in this disclosure "informed advisor" is an individual that is skilled in a particular area relating to the study of the nervous system of the individual. As a non-limiting example an informed advisor may include a medical professional who may assist and/or participate in the medical treatment of an individual's nervous system including, but not limited to, neurologists, neurosurgeons, psychiatrists, psychologists, family physicians, pediatricians, and the like thereof. As a non-limiting example input may include an informed advisor that enters a cognitive assessment comprising a brain analysis, cognitive analysis, blood analysis, urine analysis, stool analysis, saliva analysis, skin analysis, and the like thereof. Additionally or alternatively, input may include one or more medical records and/or patient charts that identify an individual's previous nervous system health such as previous memory impairments, reasoning impairments, behavior impairments, and the like thereof.

Still referring to FIG. 1, in some embodiments, computing device 104 may be configured to identify environmental factors that may negatively impact cognitive health of user as a function of cognitive indicator element 108. In a non-limiting example, computing device 104 may analyze blood to identify aluminum level, then the computing device 104 may classify the aluminum level to environmental factors using a classifier. The classifier disclosed herein may be consistent with any classifier described in the entirety of this disclosure. The classifier may be trained with environmental factor training data. Environmental factor training data may include a plurality of aluminum levels correlated to a plurality of environmental factors. This classifier may be configured to receive an aluminum level as input and to output an environmental factor. As a non-limiting example, environmental factor may include aluminum from deodorant or use of aluminum foil that may increase a risk of dementia. In some embodiments, environment factor may be obtained as a function of an environment factor directory, wherein an "environment factor directory" is a database of environment factors that may be identified as a function of analysis of one or more cognitive indicator element 108.

Still referring to FIG. 1, computing device 104 produces a cognitive appraisal 112 as a function of cognitive indicator element 108. As used in this disclosure a "cognitive appraisal" is a profile and/or estimation of an individual's cognitive health status. For example, and without limitation, cognitive appraisal 112 may denote that an individual has low and/or declined cognitive memory. As a further non-limiting example, cognitive appraisal 112 may denote that an individual has an enhanced and/or increased cognitive reasoning capability. Cognitive appraisal 112 is produced as a function of identifying a cognitive function 116. As used in this disclosure a "cognitive function" is a brain-based ability and/or skill needed in acquisition of knowledge, manipulation of information, and reasoning. For example, and without limitation cognitive function 116 may include one or more abilities and/or skills associated with perception, attention, memory, learning, decision making, language, behavior, emotions, and the like thereof. As a further non-limiting example, cognitive function 116 may include one or more abilities for visual processing, language processing, speech, and the like thereof. Cognitive function 116 may include one or more cognitive function locations, where a "cognitive function location" is a location of the brain that is responsible for performing one or more of the abilities and/or skills as described below in detail, in reference to FIG. 2. For example, and without limitation, cognitive function location may include a frontal lobe, occipital lobe, temporal lobe, parietal lobe, cerebellum, brainstem, and the like thereof.

Still referring to FIG. 1, cognitive function 116 is identified as a function of an experience label 120. As used in this disclosure an "experience label" is a label and/or identification of an individual's expected cognitive function ability and/or skill as a function of previous experience. In an embodiment, and without limitation, experience label 120 may include one or more labels of age, history, and the like thereof. For example, and without limitation, experience label 120 may identify one or more cognitive functions associated with memories of performing CPR that an individual should have as a function of being an emergency medical technician for 23 years. As a further non-limiting example, experience label 120 may identify one or more cognitive functions associated with language processing capabilities that an individual should have as a function of being a politician for 4 years. Additionally or alternatively, experience label 120 may include an expertise signature. As used in this disclosure an "expertise signature" is a profile characterizing an individual's expertise for a particular cognitive function. For example, and without limitation, expertise signature may identify that an individual who was a firefighter may have different cognitive functions when compared to an individual that is a salesman. In an embodiment, cognitive function 116 may be identified as a 32% cognitive function for a particular skill and/or ability as a function of the expected cognitive functioning due to an age of 73 years old. Additionally or alternatively, cognitive function 116 may be identified as a function of administering a cognitive examination, wherein a cognitive examination is an examination that aids in diagnosing a cognitive function of an individual, as described below in detail, in reference to FIG. 4. For example, and without limitation cognitive examinations may include one or more questionnaires, laboratory tests, mini mental state examinations. imaging examinations, and the like thereof. As a further non-limiting example, cognitive examinations may include one or cognitive tests such as the MMSE, the AMTS, the 3MS, the CASI, the Trail-making test, the MoCA, the AD-8, the IQCODE, the GDS, FAST, CDR, and the like thereof.

Still referring to FIG. 1, cognitive appraisal 112 is produced as a function of cognitive function 116 and cognitive indicator element 108 using a cognitive machine-learning model 124. Still referring to FIG. 1, computing device 104 produces cognitive appraisal 112 as a function of cognitive function 116 and cognitive indicator element 108 using a cognitive machine-learning model 120. As used in this disclosure "cognitive machine-learning model" is a machine-learning model to produce a cognitive appraisal output given cognitive functions and cognitive indicator elements as inputs; this is in contrast to a non-machine learning software program where the commands to be executed are determined in advance by a user and written in a programming language. Cognitive machine-learning model 120 may include one or more cognitive machine-learning processes such as supervised, unsupervised, or reinforcement machine-learning processes that computing device 104 and/or a remote device may or may not use in the determination of cognitive appraisal 112. As used in this disclosure "remote device" is an external device to computing device 104. A cognitive machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train cognitive machine-learning process as a function of a cognitive training set. As used in this disclosure "cognitive training set" is a training set that correlates a cognitive function and/or cognitive indicator element to a cognitive appraisal. For example, and without limitation, a cognitive function of a 40% memory capability in relation to a 63-year-old man and a cognitive indicator element enhanced SB100 protein may relate to a cognitive appraisal of low memory function. The cognitive training set may be received as a function of user-entered valuations of cognitive functions, cognitive indicator elements, and/or cognitive appraisals. Computing device 104 may receive cognitive training set by receiving correlations of cognitive functions, and/or cognitive indicator elements that were previously received and/or determined during a previous iteration of determining cognitive appraisals. The cognitive training set may be received by one or more remote devices that at least correlate a cognitive function and/or cognitive indicator element to a cognitive appraisal. As used in this disclosure "remote device" is an external device to computing device 104. The cognitive training set may be received in the form of one or more user-entered correlations of a cognitive function and/or cognitive indicator element to a cognitive appraisal. Additionally or alternatively, a user may include an informed advisor, wherein an informed advisor may include, without limitation, neurologists, neurosurgeons, psychiatrists, psychologists, family physicians, pediatricians, and the like thereof.

Still referring to FIG. 1, computing device 104 may receive cognitive machine-learning model from a remote device that utilizes one or more cognitive machine learning processes, wherein a remote device is described above in detail. For example, and without limitation, a remote device may include a computing device, external device, processor, and the like thereof. Remote device may perform the cognitive machine-learning process using the cognitive training set to generate cognitive appraisal 112 and transmit the output to computing device 104. Remote device may transmit a signal, bit, datum, or parameter to computing device 104 that at least relates to cognitive appraisal 112. Additionally or alternatively, the remote device may provide an updated machine-learning model. For example, and without limitation, an updated machine-learning model may be comprised of a firmware update, a software update, a cognitive machine-learning process correction, and the like thereof. As a non-limiting example a software update may incorporate a new cognitive function that relates to a modified cognitive indicator element. Additionally or alternatively, the updated machine learning model may be transmitted to the remote device, wherein the remote device may replace the cognitive machine-learning model with the updated machine-learning model and determine the cognitive appraisal as a function of the cognitive function using the updated machine-learning model. The updated machine-learning model may be transmitted by the remote device and received by computing device 104 as a software update, firmware update, or corrected cognitive machine-learning model. For example, and without limitation cognitive machine-learning model may utilize a random forest machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device may produce cognitive appraisal 112 as a function of a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein.

As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may identify cognitive appraisal 112 by identifying a cognitive impairment. As used in this disclosure an "cognitive impairment" is an ailment and/or collection of ailments that impact an individual's nervous system. As a non-limiting example, cognitive impairment may include Creutzfeldt-Jakob disease, Lewy body dementia, down syndrome, Alzheimer's disease, frontotemporal dementia, Huntington's disease, mixed dementia, normal pressure hydrocephalus, posterior cortical atrophy, Parkinson's disease dementia, vascular dementia, Korsakoff syndrome, traumatic brain injury, Parkinson's disease, supranuclear palsy, corticobasal degeneration, dementia due to prion disease, alcohol-related dementia, and the like thereof. Cognitive impairment may be determined as a function of one or more impairment machine-learning models. As used in this disclosure, a "impairment machine-learning model" is a machine-learning model to produce a cognitive impairment output given cognitive indicator element 108 as inputs; this is in contrast to a non-machine learning software program where the commands to be executed are determined in advance by a user and written in a programming language. Impairment machine-learning model may include one or more impairment machine-learning processes such as supervised, unsupervised, or reinforcement machine-learning processes that computing device 104 and/or a remote device may or may not use in the determination of cognitive impairment. A impairment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train impairment machine-learning process as a function of an impairment training set. As used in this disclosure, a "impairment training set" is a training set that correlates at least a cognitive enumeration and a nervous system effect to a cognitive impairment. As used in this disclosure, an "cognitive enumeration" is a measurable value associated with the cognitive indicator element. As used in this disclosure, an "nervous system effect" is an impact and/or effect the cognitive indicator element has on the nervous system of an individual. As a non-limiting example a cognitive enumeration of 17 may be relate to a nervous system effect of reduced memory capabilities wherein a cognitive impairment of Alzheimer's disease may be identified. The impairment training set may be received as a function of user-entered valuations of cognitive enumerations, nervous system effects, and/or cognitive impairments. Computing device 104 may receive impairment training set by receiving correlations of cognitive enumerations and/or nervous system effects that were previously received and/or determined during a previous iteration of determining cognitive impairments. The impairment training set may be received by one or more remote devices that at least correlate a cognitive enumeration and/or nervous system effect to a cognitive impairment, wherein a remote device is an external device to computing device 104, as described above. The impairment training set may be received in the form of one or more user-entered correlations of a cognitive enumeration and nervous system effect to a cognitive impairment. Additionally or alternatively, a user may include an informed advisor, wherein an informed advisor may include, without limitation, neurologists, neurosurgeons, psychiatrists, psychologists, family physicians, pediatricians, and the like thereof.

Still referring to FIG. 1, computing device 104 may receive impairment machine-learning model from the remote device that utilizes one or more impairment machine learning processes, wherein a remote device is described above in detail. For example, and without limitation, a remote device may include a computing device, external device, processor, and the like thereof. The remote device may perform the impairment machine-learning process using the impairment training set to generate cognitive impairment and transmit the output to computing device 104. The remote device may transmit a signal, bit, datum, or parameter to computing device 104 that at least relates to cognitive impairments. Additionally or alternatively, the remote device may provide an updated machine-learning model. For example, and without limitation, an updated machine-learning model may be comprised of a firmware update, a software update, an impairment machine-learning process correction, and the like thereof. As a non-limiting example a software update may incorporate a new cognitive enumeration that relates to a modified nervous system effect. Additionally or alternatively, the updated machine learning model may be transmitted to the remote device, wherein the remote device may replace the impairment machine-learning model with the updated machine-learning model and determine the cognitive impairment as a function of the cognitive enumeration using the updated machine-learning model. The updated machine-learning model may be transmitted by the remote device and received by computing device 104 as a software update, firmware update, or corrected impairment machine-learning model. For example, and without limitation impairment machine-learning model may utilize a Naïve bayes machine-learning process, wherein the updated machine-learning model may incorporate decision tree machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference. In an embodiment, and without limitation, impairment machine-learning model may identify cognitive impairment as a function of one or more classifiers, wherein a classifier is described above in detail.

Still referring to FIG. 1, computing device 104 determines an edible 128 as a function of cognitive appraisal 112. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. Computing device 104 may determine edible 128 as a function of receiving a nourishment composition. As used in this disclosure a "nourishment composition" is a list and/or compilation of all of the nutrients contained in an edible. As a non-limiting example nourishment composition may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition may be obtained as a function of an edible directory, wherein an "edible directory" is a database of edibles that may be identified as a function of one or more metabolic components, as described in detail below, in reference to FIG. 3.

Still referring to FIG. 1, in some embodiments, computing device 104 may determine an activity as a function of cognitive indicator element 108. As used in this disclosure, an "activity" is any action or behavior that a user may engage in. As a non-limiting example, activity may include any actions or behaviors related to exercising, sleeping, eating, snacking, energy level management, and the like. As another non-limiting example, activity may include mental activity. For example, and without limitation, mental activity may include any actions or behaviors related to stress management, mood management, or the like. As another non-limiting example, activity may include a habit. For the purposes of this disclosure, a "habit" is a routine behavior or activity that is repeated regularly. In some cases, computing device 104 may determine activity as a function of an activity goal. As used in this disclosure a "activity goal" is a recommended activity or amount or activity that a user should undertake. Activity goal may be identified by one or more organizations that relate to, represent, and/or study metabolic functions and related activities in humans, such as American Medical Association, American Society for Metabolic and Bariatric Surgery, Association of Metabolic Syndrome, The Association of Metabolic Syndrome and Urolithiasis, American College of Sports Medicine (ACSM), National Institute of Diabetes and Digestive and Kidney Diseases (NIDDK), American Diabetes Association (ADA), World Health Organization (WHO), Centers for Disease Control and Prevention (CDC), and the like thereof. In some embodiments, activity may be retrieved from database, wherein the database may be consistent with any database disclosed in the entirety of this disclosure.

Still referring to FIG. 1, computing device 104 may produce a nourishment demand as a function of cognitive appraisal 112. As used in this disclosure a "nourishment demand" is requirement and/or necessary amount of nutrients required for a user to consume. As a non-limiting example, nourishment demand may include a user requirement of 32 g of omega-3-fatty acid to be consumed per day. Nourishment demand may be determined as a function of receiving a nourishment goal. As used in this disclosure a "nourishment goal" is a recommended amount of nutrients that a user should consume. Nourishment goal may be identified by one or more organizations that relate to, represent, and/or study addictions in humans, such as the American Medical Association, American Brain Foundation, Lewy Body Dementia Association, Alzheimer's Association, Alzheimer's Drug Discovery Foundation, National Institute of Mental Health, Alzheimer's Disease Education and Referral Center, BrightFocus Foundation, National Organization for Rare Disorders, Alzheimer's Foundation of America, John Douglas French Alzheimer's Founder, and the like thereof.

Still referring to FIG. 1, computing device 104 identifies edible 128 as a function of nourishment composition, nourishment demand, and an edible machine-learning model. As used in this disclosure a "edible machine-learning model" is a machine-learning model to produce an edible output given nourishment compositions and nourishment demands as inputs; this is in contrast to a non-machine learning software program where the commands to be executed are determined in advance by a user and written in a programming language. Edible machine-learning model may include one or more edible machine-learning processes such as supervised, unsupervised, or reinforcement machine-learning processes that computing device 104 and/or a remote device may or may not use in the determination of edible 128, wherein a remote device is an external device to computing device 104 as described above in detail. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure an "edible training set" is a training set that correlates at least nourishment composition and nourishment demand to an edible. For example, and without limitation, nourishment composition of 32 mg of antioxidants and a nourishment demand of 12 mg of antioxidants as a function of a vascular dementia may relate to an edible of blackberries. The edible training set may be received as a function of user-entered valuations of nourishment compositions, nourishment demands, and/or edibles. Computing device 104 may receive edible training set by receiving correlations of nourishment compositions and/or nourishment demands that were previously received and/or determined during a previous iteration of determining edibles. The edible training set may be received by one or more remote devices that at least correlate a nourishment composition and nourishment demand to an edible, wherein a remote device is an external device to computing device 104, as described above. Edible training set may be received in the form of one or more user-entered correlations of a nourishment composition and/or nourishment demand to an edible. Additionally or alternatively, a user may include an informed advisor, wherein an informed advisor may include, without limitation, neurologists, neurosurgeons, psychiatrists, psychologists, family physicians, pediatricians, and the like thereof.

Still referring to FIG. 1, computing device 104 may receive edible machine-learning model from a remote device that utilizes one or more edible machine learning processes, wherein remote device is described above in detail. For example, and without limitation, remote device may include a computing device, external device, processor, and the like thereof. Remote device may perform the edible machine-learning process using the edible training set to generate edible 128 and transmit the output to computing device 104. Remote device may transmit a signal, bit, datum, or parameter to computing device 104 that at least relates to edible 128. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified nourishment demand. Additionally or alternatively, the updated machine learning model may be transmitted to the remote device, wherein the remote device may replace the edible machine-learning model with the updated machine-learning model and determine the edible as a function of the nourishment demand using the updated machine-learning model. The updated machine-learning model may be transmitted by the remote device and received by computing device 104 as a software update, firmware update, or corrected edible machine-learning model. For example, and without limitation an edible machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Non-provisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference. In an embodiment, and without limitation, edible machine-learning model may identify edible 128 as a function of one or more classifiers, wherein a classifier is described above in detail.

Still referring to FIG. 1, computing device 104 may identify edible as a function of a likelihood parameter. As used in this disclosure a "likelihood parameter" is a parameter that identities the probability of a user to consume an edible. As a non-limiting example likelihood parameter may identify a high probability that a user will consume an edible of chicken. As a further non-limiting example likelihood parameter may identify a low probability that a user will consume an edible of anchovies. Likelihood parameter may be determined as a function of a user taste profile. As used in this disclosure a "user taste profile" is a profile of a user that identifies one or more desires, preferences, wishes, and/or wants that a user has. As a non-limiting example a user taste profile may include a user's preference for chicken flavor and/or crunchy textured edibles. Likelihood parameter may be determined as a function of an edible profile. As used in this disclosure an "edible profile" is taste of an edible is the sensation of flavor perceived in the mouth and throat on contact with the edible. Edible profile may include one or more flavor variables. As used in this disclosure a "flavor variable" is a variable associated with the distinctive taste of an edible, wherein a distinctive may include, without limitation sweet, bitter, sour, salty, umami, cool, and/or hot. Edible profile may be determined as a function of receiving flavor variable from a flavor directory. As used in this disclosure a "flavor directory" is a database or other data structure including flavors for an edible. As a non-limiting example flavor directory may include a list and/or collection of edibles that all contain salty flavor variables. As a further non-limiting example flavor directory may include a list and/or collection of edibles that all contain sour flavor variables. Flavor directory may be implemented similarly to an edible directory as described below in detail, in reference to FIG. 3. Likelihood parameter may alternatively or additionally include any user taste profile and/or edible profile used as a likelihood parameter as described in U.S. Non-provisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, in some embodiments, computing device 104 may identify activity as a function of activity goal and cognitive indicator element 108 using an activity machine-learning model. As used in this disclosure, an "activity machine-learning model" is a machine-learning model to produce an activity output given activity goal as inputs; this is in contrast to a non-machine learning software program where the commands to be executed are determined in advance by a user and written in a programming language. Activity machine-learning model may include one or more activity machine-learning processes such as supervised, unsupervised, or reinforcement machine-learning processes that computing device 104 and/or a remote device may or may not use in the determination of activity.

Still referring to FIG. 1, computing device 104 may train activity machine-learning process as a function of an activity training set. As sued in this disclosure, an "activity training set is a training set that correlates cognitive indicator element 108 to an activity. For example, and without limitation, activity goal of and cognitive indicator element 108 of datum from one or more devices that collect, store, and/or calculate voltages and currents that are associated with the user's nervous system may relate to activity of mental exercise. The activity training set may be received as a function of user-entered valuations of activity goals and/or activities. Additionally or alternatively, a user may include an informed advisor, wherein an informed advisor may include, without limitation, endocrinologists, metabolic physicians, functional medicine practitioners, chemical pathologists, cardiovascular physicians, family physicians, family physicians, and the like thereof. Computing device 104 may receive activity training set by receiving correlations of activity goals and/or cognitive indicator elements 108 that were previously received and/or determined during a previous iteration of determining activities. The activity training set may be received by one or more remote devices that at least correlate activity goal and/or cognitive indicator element 108 to activity, wherein a remote device is an external device to computing device 104, as described above.

Still referring to FIG. 1, computing device 104 generates a nourishment program 132 as a function of edible 128. Still referring to FIG. 1, computing device 104 generates a nourishment program 132 as a function of edible 128. As used in this disclosure a "nourishment program" is a program consisting of one or more edibles that are to be consumed over a given time period, wherein a time period is a temporal measurement such as seconds, minutes, hours, days, weeks, months, years, and the like thereof. As a non-limiting example nourishment program 132 may consist of recommending red meat for 4 days. As a further non-limiting example nourishment program 132 may recommend fish for a first day, broccoli for a second day, and legumes for a third day. Nourishment program 132 may include one or more diet programs such as paleo, keto, vegan, vegetarian, and the like thereof. In a non-limiting example, nourishment program 132 may include cutting sugar or processed food out of diet. In a non-limiting example, nourishment program 132 may include optimization of gut microbiome. For example, and without limitation, nourishment program 132 may include fiber intake, probiotic supplement, minimizing antibiotic use, stress management, sleep management, or the like. This reversal of gut dysfunction, in a non-limiting example, may improve cognitive health and function. Computing device 104 may develop nourishment program 132 as a function of an intended outcome. As used in this disclosure an "intended outcome" is an outcome that an edible may generate according to a predicted and/or purposeful plan. For example, and without limitation, intended outcome may include optical cognitive function. For example, and without limitation, intended outcome may include improve brain plasticity. As a non-limiting example, intended outcome may include a treatment outcome. As used in this disclosure a "treatment outcome" is an intended outcome that is designed to at least reverse and/or eliminate cognitive appraisal 112, cognitive indicator element 108 and/or cognitive disorder. As a non-limiting example, a treatment outcome may include reversing the effects of the cognitive disorder vascular dementia. As a further non-limiting example, a treatment outcome includes reversing the cognitive disorder of Lewy body dementia. As another non-limiting example, treatment outcome may include reducing neuroinflammation. Intended outcome may include a prevention outcome. As used in this disclosure a "prevention outcome" is an intended outcome that is designed to at least prevent and/or avert cognitive appraisal 112, cognitive indicator element 108 and/or cognitive disorder. As a non-limiting example, prevention outcome may include reducing neurodegeneration. As a non-limiting example, a prevention outcome may include preventing the development of the cognitive disorder Creutzfeldt Jakob disease. As a further non-limiting example a prevention outcome may include preventing the development of Alzheimer's Disease as a function of a Mediterranean diet. As a further non-limiting example, prevention outcome may include preventing cognitive decline and/or cognitive impairment as a function of recommending edibles such as grapes, blueberries, cilantro, chocolate, and the like thereof. Intended outcome may include a mitigating outcome. As used in this disclosure a "mitigating outcome" is an intended outcome that is designed to slow and/or mitigate the developed of cognitive appraisal 112, cognitive indicator element 108 and/or cognitive disorder. As a non-limiting example, a mitigating outcome may include slowing down the development of the cognitive disorder frontotemporal dementia. As another non-limiting example, mitigating outcome may include reversal of gut dysfunction, which may aid in improving cognitive health and function.

Still referring to FIG. 1, in some embodiments, computing device 104 may generate a life style program as a function of activity, cognitive indicator element 108, an activity outcome and activity outcome item. As a non-limiting example, computing device 104 may identify a keyword of cognitive indicator element 108 and activity outcome, then match activity and activity outcome item to life style program as a function of the keyword. For the purposes of this disclosure, a "keyword" is an element of word or syntax used to identify and/or match elements to each other. In some embodiments, computing device 104 may find keyword of cognitive indicator element 108 and/or activity outcome using an optical character recognition (OCR). As a non-limiting example, if cognitive indicator element 108 includes low brain activity and activity outcome includes increasing brain activity, a keyword of cognitive indicator element 108 may include low, brain, activity or brain activity and a keyword of the activity outcome may include increase, brain, activity or brain activity. For example, and without limitation, after identifying the keywords, computing device 104 may match cognitive indicator element 108 and activity outcome using the keywords and relate activity and activity outcome item related to the cognitive indicator element 108 and the activity outcome to generate lift style program.

Still referring to FIG. 1, for the purposes of this disclosure, an "activity outcome" is an outcome that an activity may generate according to a predicted and/or purposeful plan. As a non-limiting example, activity outcome may include a treatment outcome, mitigating outcome or a prevention outcome as described above. For example, and without limitation, treatment outcome may include increasing brain activity. For example, and without limitation, mitigating outcome may include reducing aluminum level. For example, and without limitation, prevention outcome may include increasing brain activity. In some embodiments, activity outcome may include activity outcome item. For the purposes of this disclosure, "activity outcome item" is a task or activity that can be or should be done to achieve activity outcome. As a non-limiting example, activity outcome item may include a list of mental exercises to increase brain activity. As another non-limiting example, activity outcome item may include a list of tasks to reduce aluminum level. In some embodiments, activity outcome item may include edible 128. As another non-limiting example, activity outcome item may include a list of tasks and edible 128 to increasing brain activity. As another non-limiting example, activity outcome item may include a list of tasks and edibles 128 to reduce aluminum level. In some embodiments, activity outcome item may be consistent with activity goal. In some embodiments, activity outcome item may be obtained from an activity directory. As used in this disclosure a "activity directory" is a database of activity outcome item. In some embodiments, activity outcome item may be obtained from user. As a non-limiting example, user may include an informed advisor, wherein an informed advisor may include, without limitation, endocrinologists, metabolic physicians, functional medicine practitioners, chemical pathologists, cardiovascular physicians, family physicians, family physicians, and the like thereof. In some cases, life style program may improve user's metabolic system, nervous system, or the like.

Still referring to FIG. 1, computing device 104 may develop nourishment program 132 as a function of edible 128 and intended outcome using a nourishment machine-learning model. As used in this disclosure a "nourishment machine-learning model" is a machine-learning model to produce a nourishment program output given edibles and/or intended outcomes as inputs; this is in contrast to a non-machine learning software program where the commands to be executed are determined in advance by a user and written in a programming language. Nourishment machine-learning model may include one or more nourishment machine-learning processes such as supervised, unsupervised, or reinforcement machine-learning processes that computing device 104 and/or a remote device may or may not use in the development of nourishment program 132. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, in some embodiments, nourishment program 132 may incorporate an integrative therapy to aid in brain health. For the purposes of this disclosure, an "integrative therapy" is a therapy that combines and integrates different therapeutic techniques. As a non-limiting example, integrative therapy may include herbal medicine, acupuncture, moxibustion, cupping, aromatherapy, or the like. As another non-limiting example, integrative therapy may include pharmaceutical medication, surgical intervention, or the like. In some embodiments, nourishment program 132 may incorporate a life style program. In some embodiments, computing device 104 may generate life style program. For the purposes of this disclosure, a "life style program" is a program consisting of one or more activities that are to be undertaken over a given time period. As a non-limiting example, the time period may include a temporal measurement such as seconds, minutes, hours, days, weeks, months, years, and the like thereof. As a non-limiting example, life style program may consist of recommending running three times a week. As a further non-limiting example, life style program may recommend reducing snacks between meals. As another non-limiting example, life style program may consist modifying sleeping habit every day. In some cases, life style program may prevent, improve or treat user's metabolic system. In some cases, life style program may prevent, improve or treat user's cognitive disorder. Persons skilled in the art, upon reviewing the entirety of this disclosure, may appreciate various life style programs that can be generated by system 100.

Still referring to FIG. 1, in some embodiments, computing device 104 may

Still referring to FIG. 1, computing device 104 may train nourishment machine-learning process as a function of a nourishment training set. As used in this disclosure a "nourishment training set" is a training set that correlates an intended outcome to an edible. The nourishment training set may be received as a function of user-entered edibles, intended outcomes, and/or nourishment programs. For example, and without limitation, an intended outcome of treating Parkinson's disease may correlate to an edible of blueberries and/or blackberries. Computing device 104 may receive nourishment training by receiving correlations of intended outcomes and/or edibles that were previously received and/or determined during a previous iteration of developing nourishment programs. The nourishment training set may be received by one or more remote devices that at least correlate an intended outcome and/or edible to a nourishment program, wherein a remote device is an external device to computing device 104, as described above. Nourishment training set may be received in the form of one or more user-entered correlations of an intended outcome and/or edible to a nourishment program. Additionally or alternatively, a user may include an informed advisor, wherein an informed advisor may include, without limitation, neurologists, neurosurgeons, psychiatrists, psychologists, family physicians, pediatricians, and the like thereof.

Still referring to FIG. 1, computing device 104 may receive nourishment machine-learning model from the remote device that utilizes one or more nourishment machine learning processes, wherein a remote device is described above in detail. For example, and without limitation, a remote device may include a computing device, external device, processor, and the like thereof. The remote device may perform the nourishment machine-learning process using the nourishment training set to develop nourishment program 132 and transmit the output to computing device 104. The remote device may transmit a signal, bit, datum, or parameter to computing device 104 that at least relates to nourishment program 132. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new intended outcome that relates to a modified edible. Additionally or alternatively, the updated machine learning model may be transmitted to the remote device, wherein the remote device may replace the nourishment machine-learning model with the updated machine-learning model and develop the nourishment program as a function of the intended outcome using the updated machine-learning model. The updated machine-learning model may be transmitted by the remote device and received by computing device 104 as a software update, firmware update, or corrected nourishment machine-learning model. For example, and without limitation nourishment machine-learning model may utilize a neural net machine-learning process, wherein the updated machine-learning model may incorporate decision tree machine-learning processes.

With continued reference to FIG. 1, computing device 104 may be configured to receive a cognitive response of a user as a function of implementing a nourishment program 132. As used in this disclosure a "cognitive response" is a response from the user regarding the efficacy of nourishment program 132. Cognitive response may include any information about nourishment program 132. For example, and without limitation, cognitive response may include a user's consistency with nourishment program 132. As a further non-limiting example, cognitive response may include one or more cognitive assessment improvements and/or cognitive examination improvements. For example, and without limitation, computing device 104 may track patterns of improvement in user over time. In a non-limiting example, patterns of improvement can be used to identify which nourishment program 132 affects user most profoundly. As a further non-limiting example, cognitive response may include one or more user preferences, likes and/or dislikes of nourishment program 132. Cognitive response may also describe a user's current feelings and/or opinions of nourishment program 132. Cognitive response may describe a user's psychiatric condition and/or psychiatric disease is better controlled and/or maintained as a function of one or more third-party evaluations. Computing device 104 may update a nourishment program 128 based on a cognitive response. Updating nourishment program 132 may include any method as described above in detail for generating nourishment program 132.

Figure 2:
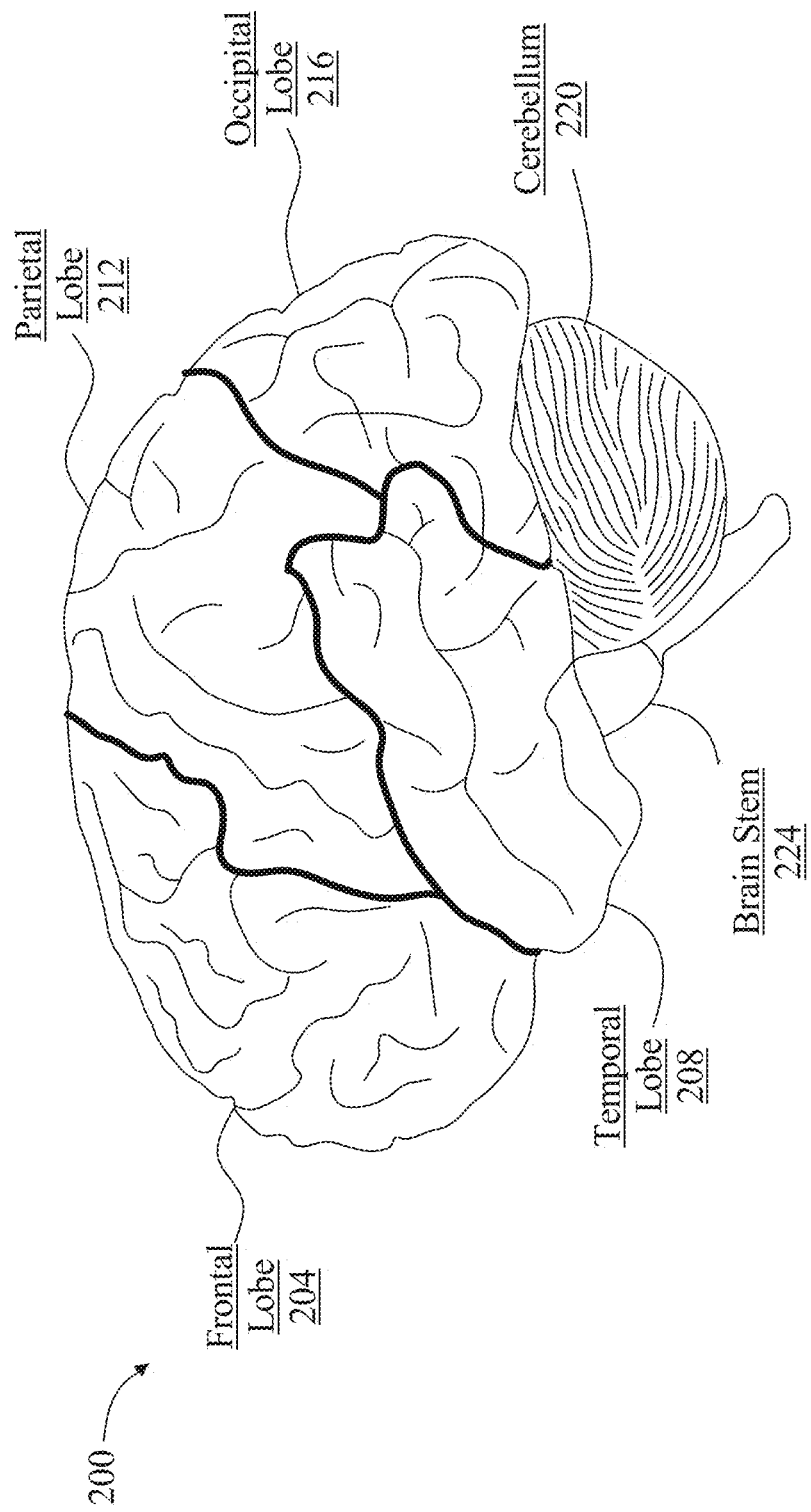
FIG. 2 is a block diagram of an exemplary embodiment of a cognitive function location according to an embodiment of the invention.

Now referring to FIG. 2, an exemplary embodiment 200 of a cognitive function location is illustrated. Cognitive function location may include a frontal lobe 204. As used in this disclosure a "frontal lobe" is location of the brain located at the front of each cerebral hemisphere and positioned in front of the parietal lobe and above in front of the temporal lobe. As a non-limiting example, frontal lobe 204 may be separated from the parietal lobe by a central sulcus. As a further non-limiting example, frontal lobe 204 may be separated from the temporal love by a lateral sulcus. Frontal lobe 204 may include one or more locations that contain most of the dopamine-delicate neurons in the cerebral context. As a further non-limiting example frontal lobe 404 may include one or more prefrontal cortexes, wherein a prefrontal cortex is a location of the brain that may relate to long-term and/or short-term memories. Cognitive function location may include a temporal lobe 208. As used in this disclosure a "temporal lobe" is a location of the brain that is located beneath the lateral fissure on both cerebral hemispheres of a brain. Temporal lobe 408 may include, without limitation a location of the brain that is involved in processing sensory input into derived meanings for the appropriate retention of visual memories, language comprehension, and emotion association. As a non-limiting example, temporal lobe 408 may include an area of the brain such as the hippocampus, wherein the hippocampus is a cognitive function location associated with forming new memories and learning new things.

Still referring to FIG. 2, cognitive function location may include a parietal lobe 212. As used in this disclosure a "parietal lobe" location of the brain located above the occipital love and behind the frontal lobe and central sulcus. Parietal lobe 212 may include a location of the brain that integrates sensory information among various modalities, including spatial sense and/or proprioception, mechanoreception, and/or any other sensory receptors. Cognitive function location may include an occipital lobe 216. As used in this disclosure an "occipital lobe" is a location of the brain located behind the parietal lobe and temporal lobe and just above the cerebellum. For example, and without limitation, occipital lobe 216 may include a location associated with a visual processing center of the brain. Cognitive function location may include a cerebellum 220. As used in this disclosure a "cerebellum" is a location of the brain located below the occipital lobe. Cerebellum 220 may include one or more locations in the brain responsible for motor control, attention, language, and emotional control. Cognitive function may include a brain stem 224. As used in this disclosure a "brain stem" is a location of the brain located below the temporal lobe and in front of the cerebellum. Brain stem 224 may include one or more locations responsible for regulating cardiac function and/or respiratory function. In an embodiment, brain stem 224 may include one or more locations responsible for the regulation of the central nervous system and/or the sleep cycle of the body.

Figure 3:
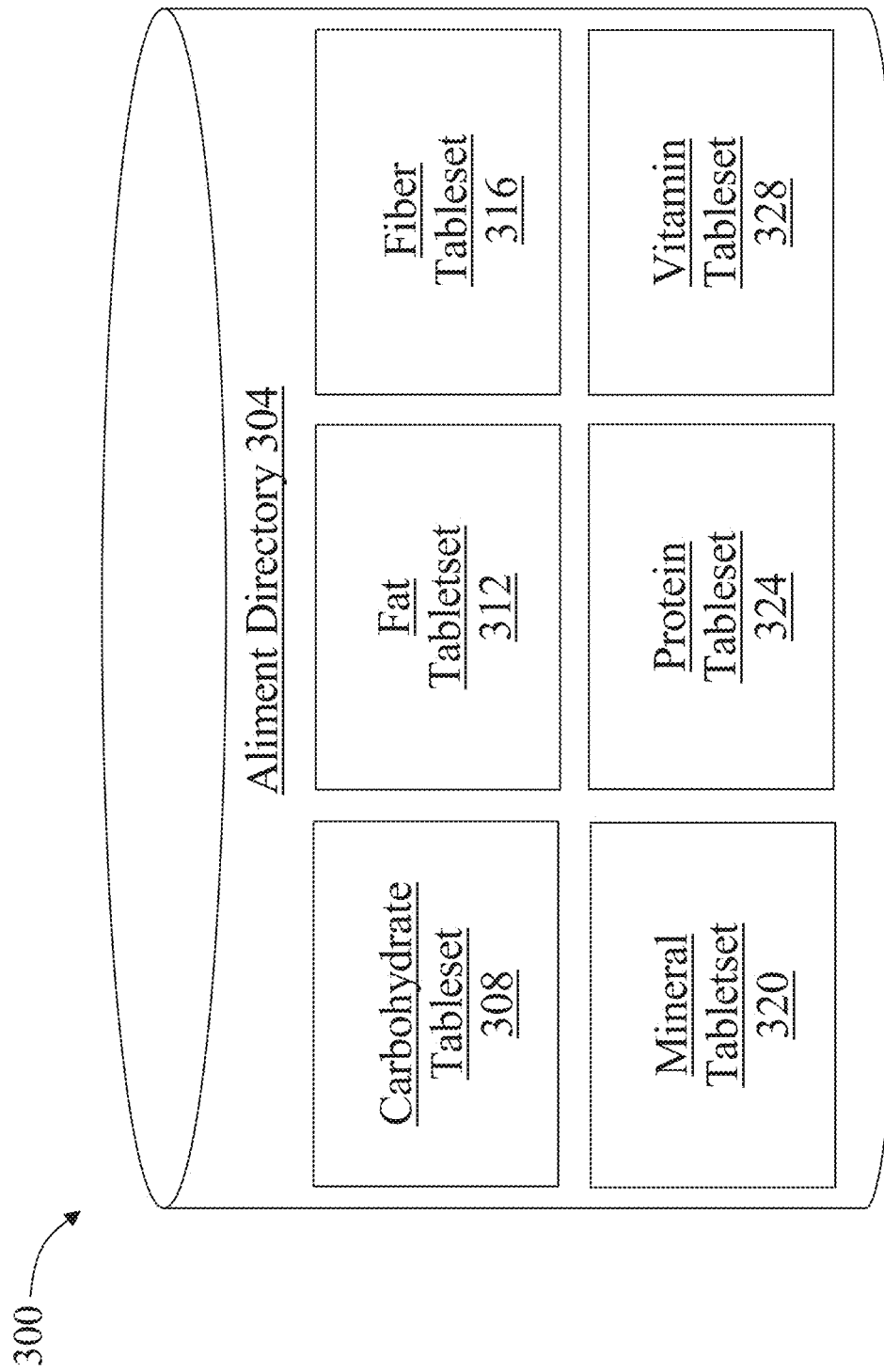
FIG. 3 is a block diagram of an exemplary embodiment of an edible directory according to an embodiment of the invention.

Now referring to FIG. 3, an exemplary embodiment 300 of an edible directory 304 according to an embodiment of the invention is illustrated. Edible directory 304 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 304 may alternatively or additionally be implemented using a distributed data storage protocol and/or data structure, such as a distributed hash table or the like. Edible directory 304 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 304 may include a carbohydrate tableset 308. Carbohydrate tableset 308 may relate to a nourishment composition of an edible with respect to the quantity and/or type of carbohydrates in the edible. As a non-limiting example, carbohydrate tableset 308 may include monosaccharides, disaccharides, oligosaccharides, polysaccharides, and the like thereof. Edible directory 304 may include a fat tableset 312. Fat tableset 312 may relate to a nourishment composition of an edible with respect to the quantity and/or type of esterified fatty acids in the edible. Fat tableset 312 may include, without limitation, triglycerides, monoglycerides, diglycerides, phospholipids, sterols, waxes, and free fatty acids. Edible directory 304 may include a fiber tableset 316. Fiber tableset 316 may relate to a nourishment composition of an edible with respect to the quantity and/or type of fiber in the edible. As a non-limiting example, fiber tableset 316 may include soluble fiber, such as beta-glucans, raw guar gum, psyllium, inulin, and the like thereof as well as insoluble fiber, such as wheat bran, cellulose, lignin, and the like thereof. Edible directory 304 may include a mineral tableset 320. Mineral tableset 320 may relate to a nourishment composition of an edible with respect to the quantity and/or type of minerals in the edible. As a non-limiting example, mineral tableset 320 may include calcium, phosphorous, magnesium, sodium, potassium, chloride, sulfur, iron, manganese, copper, iodine, zing, cobalt, fluoride, selenium, and the like thereof. Edible directory 304 may include a protein tableset 324. Protein tableset 324 may relate to a nourishment composition of an edible with respect to the quantity and/or type of proteins in the edible. As a non-limiting example, protein tableset 324 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 304 may include a vitamin tableset 328. Vitamin tableset 328 may relate to a nourishment composition of an edible with respect to the quantity and/or type of vitamins in the edible. As a non-limiting example, vitamin tableset 328 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
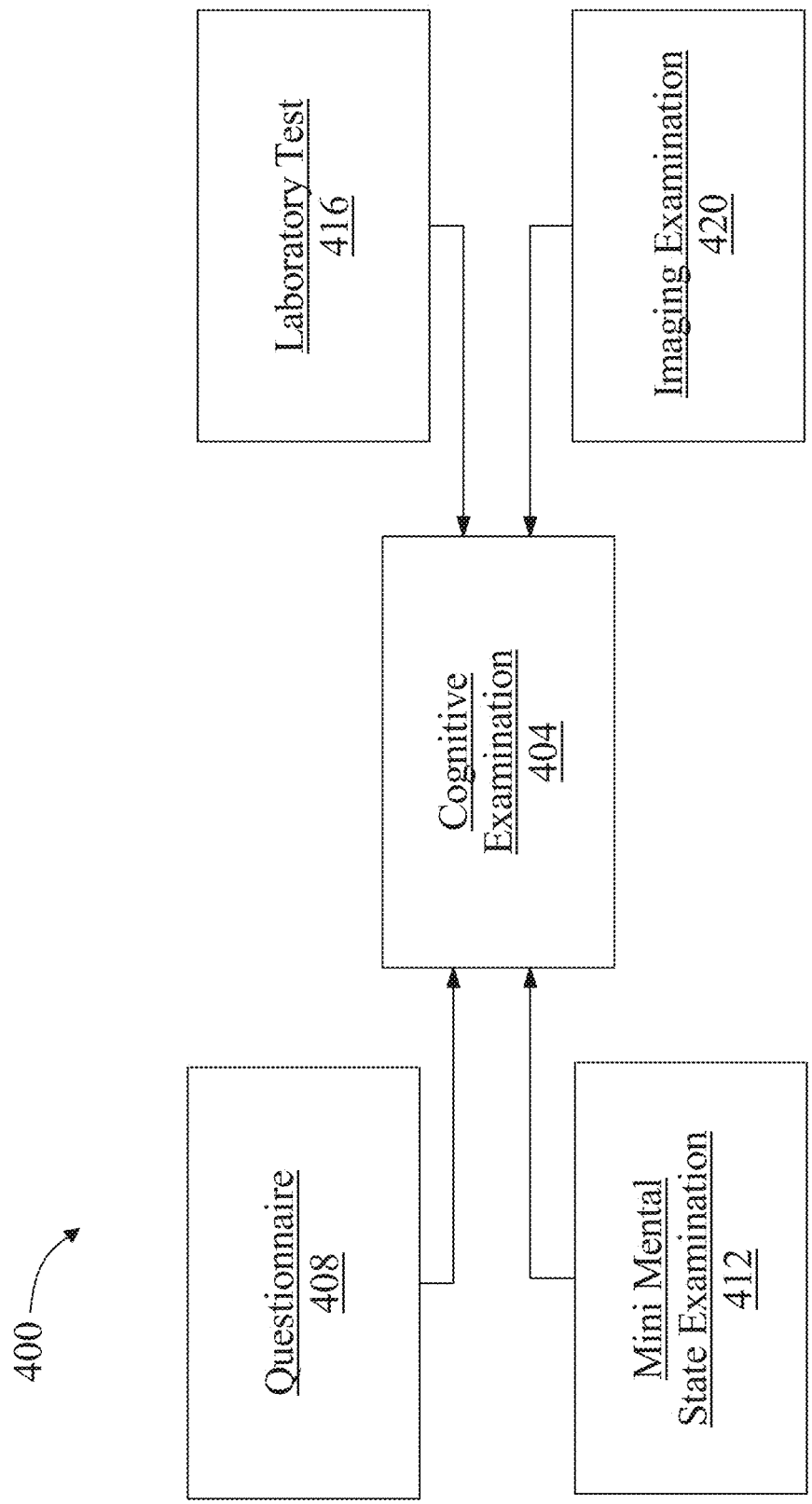
FIG. 4 is a block diagram of an exemplary embodiment of a cognitive examination according to an embodiment of the invention.

Referring now to FIG. 4, an exemplary embodiment 400 of a cognitive examination 404 is illustrated. As used in this disclosure a "cognitive examination" is an examination that aids in diagnosing a cognitive function of an individual. In an embodiment and without limitation, cognitive examination may aid in identifying one or more cognitive functions such as delirium, agitation, restlessness, aggression, hallucinations, delusions, apathy, anxiety, and the like thereof. Cognitive examination 404 may include a questionnaire 408. As used in this disclosure a "questionnaire" is a list and/or set of printed or written questions with a choice of answers that aid in diagnosing cognitive function 116. For example, and without limitation questionnaire 408 may include a/an AD-8 screening questionnaire, informant questionnaire, cognitive decline in the elderly questionnaire, Alzheimer's disease caregiver questionnaire, general practitioner assessment of cognition questionnaire, and the like thereof. Cognitive examination 404 may include a mini mental state examination 412. As used in this disclosure a "mini mental state examination" is an examination that aids in diagnosing one or more cognitive functions of an individual. Mini mental state examination 412 may include one or more assessments of a person's personality, activity capabilities, and/or behavior. For example, and without limitation mini mental state examination 412 may include a/an abbreviated mental test score, modified mini mental state examination, cognitive abilities screening instrument, trail-making test, clock drawing test, Montreal cognitive assessment, and the like thereof. Cognitive examination 404 may include a laboratory test 416. As used in this disclosure a "laboratory test" is a test and/or analysis performed by an informed advisor. For example, and without limitation, laboratory test 416 may include one or more blood tests. As a further non-limiting example, laboratory test 416 may include one or more tests capable of monitoring vitamin B12, folic acid, thyroid-stimulating hormone, c-reactive protein, full blood count, electrolytes, calcium, renal function, liver enzymes, and the like thereof. Cognitive examination 404 may include an imaging examination 420. As used in this disclosure an "imaging examination" is one or more examinations that aid in determining cognitive function 116 as a function of an imaging device. For example, and without limitation, imaging examination 420 may include one or more CT scan examination, MRI examinations, neuroimaging examinations, SPECT examinations, PET examinations, PIB-PET examinations, carbon-11-dihydrotetrabenazine examinations, and the like thereof.

Figure 5:
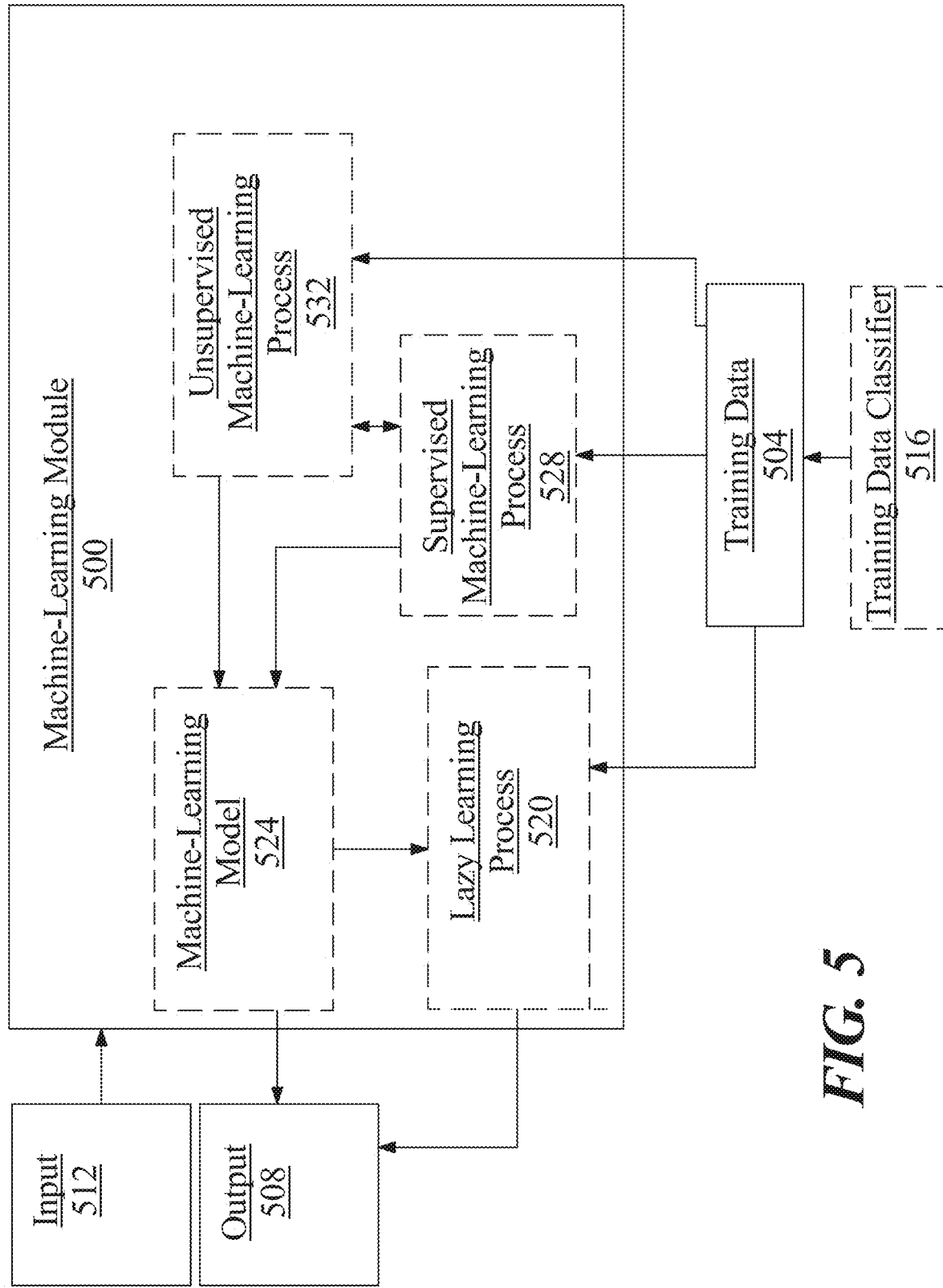
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data.

Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs of cognitive functions and/or cognitive indicator elements may output cognitive appraisals.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to sub-categories of cognitive functions such as cognitive function locations, wherein a cognitive function location is described above, in reference to FIGS. 1-2.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include cognitive functions and/or cognitive indicator elements as described above as inputs, cognitive appraisals as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
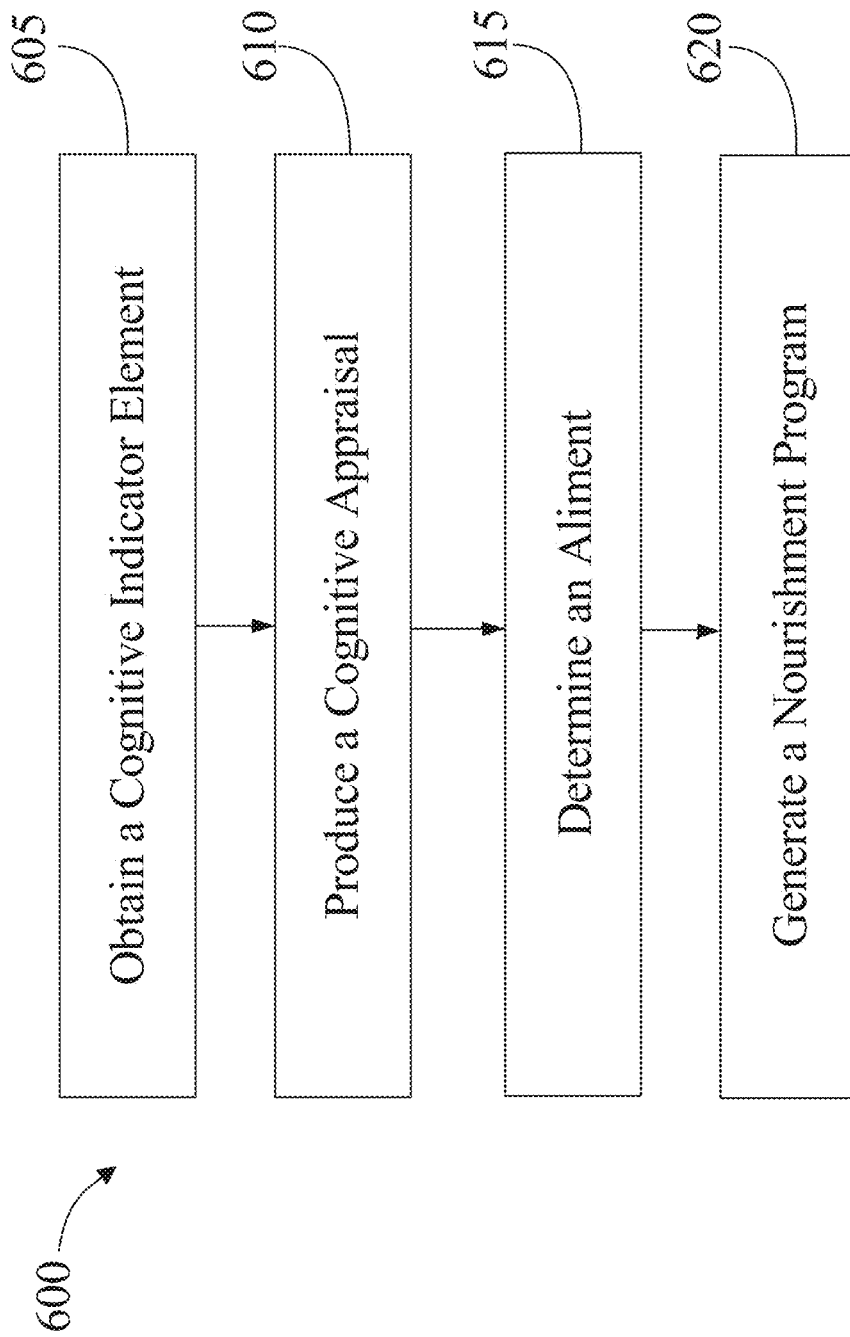
FIG. 6 is a process flow diagram illustrating an exemplary embodiment of a method of generating an addiction nourishment program.

Now referring to FIG. 6, an exemplary embodiment of a method 600 for generating a cognitive disorder nourishment program is illustrated. At step 605, a computing device 104 obtains a cognitive indicator element 108. Computing device 104 includes any of the computing device 104 as described above, in reference to FIGS. 1-5. Cognitive indicator element 108 includes any of cognitive indicator element 108 as described above, in reference to FIGS. 1-5.

Still referring to FIG. 6, at step 610, computing device 104 produces a cognitive appraisal 112 as a function of cognitive indicator element 108. Cognitive appraisal 112 includes any of cognitive appraisal 112 as described above, in reference to FIGS. 1-5. Cognitive appraisal 112 is produced as a function of identifying a cognitive function 116. Cognitive function 116 includes any of cognitive function 116 as described above, in reference to FIGS. 1-5. Cognitive function 116 is identified as a function of an experience label 120. Experience label 120 includes any of experience label 120 as described above, in reference to FIGS. 1-5. Cognitive appraisal 112 is produced as a function of cognitive function 116 and cognitive indicator element 108 using a cognitive machine-learning model 124. Cognitive machine-learning model 124 includes any of cognitive machine-learning model 124 as described above, in reference to FIGS. 1-5.

Still referring to FIG. 6, at step 615, computing device 104 determines an edible 128 as a function of cognitive appraisal 112. Edible 128 includes any of edible !!7 as described above, in reference to FIGS. 1-5.

Still referring to FIG. 6, at step 620, computing device 104 generates a nourishment program 132 as a function of edible 128. Nourishment program 132 includes any nourishment program 132 as described above, in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
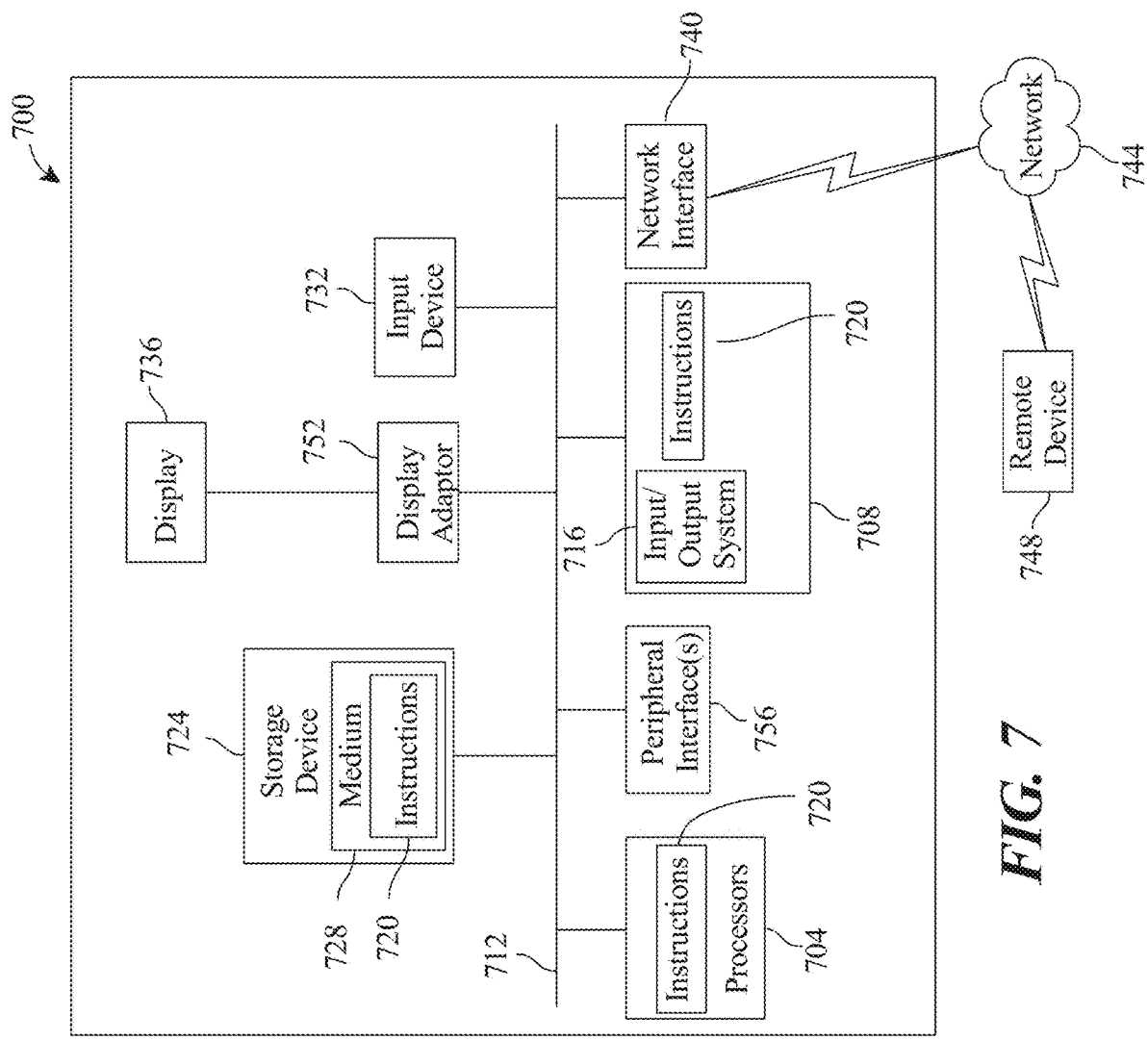
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a cognitive disorder nourishment program, the system comprising:
   a computing device, the computing device comprises:
   a processor and a memory and is configured to:
   obtain a cognitive indicator element;
   determine an edible as a function of the cognitive indicator element;
   generate a nourishment program as a function of the edible;
   receive a cognitive response of a user as a function of implementing the nourishment program;
   update the nourishment program as a function of the cognitive response;
   receiving a nourishment composition from an edible directory;
   producing a nourishment demand as a function of the cognitive appraisal; and
   determining the edible as a function of the nourishment composition and the nourishment demand using an edible machine-learning model;
   replace the edible machine-learning model with an updated machine-learning model using a remote device; and
   determine the edible as a function of the nourishment demand using the updated machine-learning model.

2. The system of claim 1, wherein the cognitive indicator element comprises chemicals that are associated with a user's nervous system.

3. The system of claim 1, wherein obtaining the cognitive indicator element further comprises identifying a cognitive assessment and obtaining the cognitive indicator element as a function of the cognitive assessment.

4. The system of claim 1, wherein generating the nourishment program further comprises:
   receiving an intended outcome; and
   generating the nourishment program as a function of the intended outcome using a nourishment machine-learning model.

5. The system of claim 4, wherein the computing device is further configured to:
   replace the nourishment machine-learning model with the updated machine-learning model using the remote device; and
   develop the nourishment program as a function of the intended outcome using the updated machine-learning model,
   update the nourishment program as a function of the cognitive response.

6. The system of claim 1, wherein the cognitive response comprises one or more cognitive examination improvements, wherein the one or more cognitive examination improvements comprises imaging examination.

7. The system of claim 1, wherein the nourishment program identifies a lifestyle improvement.

8. The system of claim 1, wherein the computing device is further configured to:
   determine an activity as a function of the cognitive indicator element; and
   generate a life style program of the nourishment program as a function of the activity.

9. A method for generating a cognitive disorder nourishment program, the method comprising:
   obtaining, by a computing device, a cognitive indicator element;
   determining, by the computing device, an edible as a function of the cognitive indicator element;
   generating, by the computing device, a nourishment program as a function of the edible
   receiving, by the computing device, a cognitive response of a user as a function of implementing the nourishment program;
   updating, by the computing device, the nourishment program as a function of the cognitive response;

receiving a nourishment composition from an edible directory;
producing a nourishment demand as a function of the cognitive appraisal; and
determining the edible as a function of the nourishment composition and the nourishment demand using an edible machine-learning model;
replacing, using the computing device and a remote device, the edible machine-learning model with an updated machine-learning model; and
determining, using the computing device and the remote device, the edible as a function of the nourishment demand using the updated machine-learning model.

10. The method of claim 9, wherein the cognitive indicator element comprises chemicals that are associated with a user's nervous system.

11. The method of claim 9, wherein obtaining the cognitive indicator element further comprises identifying a cognitive assessment and obtaining the cognitive indicator element as a function of the cognitive assessment.

12. The method of claim 9, wherein generating the nourishment program further comprises:
receiving an intended outcome; and
generating the nourishment program as a function of the intended outcome using a nourishment machine-learning model.

13. The method of claim 12, further comprising:
replacing, using the computing device and the remote device, the nourishment machine-learning model with the updated machine-learning model; and
developing, using the computing device and the remote device, the nourishment program as a function of the intended outcome using the updated machine-learning model.

14. The method of claim 9, wherein the cognitive response comprises one or more cognitive examination improvements, wherein the one or more cognitive examination improvements comprises imaging examination.

15. The method of claim 9, wherein the nourishment program identifies a lifestyle improvement.

16. The method of claim 9, further comprising:
determining, using the computing device, an activity as a function of the cognitive indicator element; and
generating, using the computing device, a life style program of the nourishment program as a function of the activity.

* * * * *